US006469169B1

(12) United States Patent
Seayad et al.

(10) Patent No.: US 6,469,169 B1
(45) Date of Patent: Oct. 22, 2002

(54) WATER SOLUBLE PALLADIUM COMPLEXES AND PROCESS FOR THE PREPARATION THEREOF

(75) Inventors: Jayasree Seayad, Pune (IN); Abdul Majeed Seayad, Pune (IN); Bibhas Ranjan Sarkar, Pune (IN); Raghunath Vitthal Chaudhari, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/813,098

(22) Filed: Mar. 20, 2001

(51) Int. Cl.$^7$ ............................ C07F 15/00; B01J 31/00
(52) U.S. Cl. .................... 546/2; 546/5; 546/7; 556/23
(58) Field of Search ........................... 546/25.7; 556/23

(56) References Cited

U.S. PATENT DOCUMENTS 6,069,253 A * 5/2000 Chaudhari et al. .............. 546/2

OTHER PUBLICATIONS

Okunaka et al, Bull. Chem. Soc. Japan, vol. 50, No. 4 p. 907–909, 1977.*

* cited by examiner

Primary Examiner—Zinna Northington Davis
(74) Attorney, Agent, or Firm—Ladas & Parry

(57) ABSTRACT

The invention provides a water soluble palladium complex of the general formula I

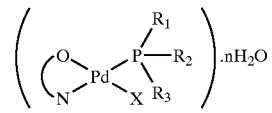

Formula I wherein $R_1$, $R_2$, $R_3$ are substituents on phosphine ligands selected from the group consisting of hydrogen, alkyl, arylalkyl, and cycloaliphatic at least one of which carries a sulfonic acid, and salts thereof, X is aryl or alkyl sulphonato or aryl or alkyl carboxylato or formato or halides such as $Cl^-$, $Br^-$, $I^-$

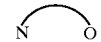

is an anionic chelating ligand consisting of an N donor and a $O^-$ group, $1<n<10$ and a process for the preparation thereof.

15 Claims, No Drawings

WATER SOLUBLE PALLADIUM COMPLEXES AND PROCESS FOR THE PREPARATION THEREOF

FIELD OF THE INVENTION

The present invention relates to novel water-soluble palladium complexes and a process for the preparation thereof More particularly, the present invention relates to a water soluble palladium complex of the general formula 1,

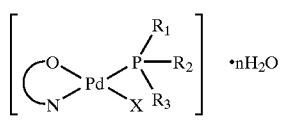

Formula I being an anionic chelating ligand containing an N donor and a O$^-$ group, wherein $R_1$, $R_2$ and $R_3$ are substituents of phosphine ligand at least one of which carries a sulfonic acid or salt there of and X is a sulfonato, carboxylato or formato group, or any of the halides; a process for the preparation thereof and supported aqueous phase catalysts thereof The water soluble palladium complexes and supported aqueous phase catalysts prepared by the process of the present invention are useful as efficient catalysts for reactions such as carbonylation, oxidation, hydrogenation, coupling, alkylation, oligomerization, polymerisation etc.

BACKGROUND OF THE INVENTION

Water-soluble palladium complexes play an important role as catalysts for several organic transformations. One method in which such water-soluble catalysts can be used is in biphasic systems; comprising the water soluble organo-metallic complex catalyst in aqueous phase and the organic reactants and products as a water immiscible phase; thereby providing easy separation and reuse of the,catalyst owing to the immiscibility of the catalyst phase with the organic substrates and products (U.S. Pat. No. 31812; Kuntz E.G. CHEMTECH 17, 1987, 570; EP 0107006; B. Cornils, W. A. Herrmann (Eds.), Aqueous-Phase Organometallic Catalysis, Wiley-VCH, 1998, Weinheim.) Another approach is as supported aqueous phase catalysts (U.S. Pat. No. 5,736,980, U.S. Pat. No. 5,935,892) in which the catalytic material consists of a thin aqueous film containing the water-soluble metal complex catalyst spread over a high-surface-area inorganic support, such as silica (J. P. Arhancet, M. E. Davis, J. S. Merola, Be. Hanson, Nature, 339, 1989, 454; K. T. Wan, M. E. Davis, Nature, 370, 1994, 449; KIT. Wan, M. E. Davis, J. Catal., 148, 1994, 1).

U.S. Pat. No. 6,069,253 discloses the preparation of an anionic chelating. ligand containing a N donor and O$^-$ group.

OBJECTS OF THE INVENTION

The main object of the present invention is to provide novel water-soluble palladium complexes and supported aqueous phase catalysts thereof that areuseful catalysts for a variety of organic transformations such as carbonylation, oxidation, hydrogenation, coupling, alkylation, oligomerization, polymerisation etc.

It is another object of the invention to provide a process for the preparation of novel water soluble palladium complexes that are useful as catalysts for a variety of organic transformations.

SUMMARY OF THE INVENTION

The present invention also relates to a process for the preparation of water soluble palladium complexes having general formula I,

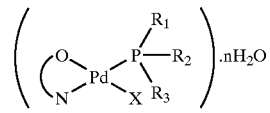

Formula I wherein $R_1$, $R_2$, and $R_3$ are substituents on phosphine ligands selected from the group consisting of hydrogen, alkyl, arylakyl, and cycloaliphatic at least one of which carries a sulfonic acid, and salts thereof, X is aryl or alkyl sulphonato or aryl or alkyl carboxylato or formato or halide such as Cl$^-$, Br$^-$, or I$^-$, N∩O is an anionic chelating ligand consisting of an N donor and a O$^-$ group, and 1<n<10, said process comprising reacting a palladium compound of formula II

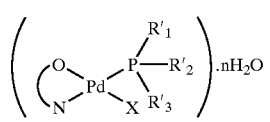

Formula II wherein $R'_1$, $R'_2$, and $R'_3$ are substituents on phosphine ligands such as, alkyl, aryl, arylalkyl, or cycloaliphatic, X is aryl or alkyl sulphonato or aryl or alkyl carboxylato or formato or halides such as Cl$^-$, Br$^-$, I$^-$,

is an anionic chelating ligand containing a N donor and O$^-$ group, in an organic solvent with a sulfonated phosphine ligand in degassed water to form the palladium complex of formula I in water, separating the aqueous layer and precipitating the complex of formula I by adding an alcohol solvent.

In one embodiment of the invention, the precipitated complex of formula I is converted into the supported aqueous phase form by mixing the aqueous layer containing the water soluble palladium complex of formula I with dehydroxylated silica in a Schlenk flask, forming a wet solid, stirring the wet solid vigorously for 2 h under argon, evaporating water under high vacuum at constant stirring to obtain the supported aqueous phase catalyst containing the palladium complex of the formula I as a dry yellow powder.

In another embodiment of the invention, the anionic chelating ligand in the compounds of formula I and II is an organic compound, containing a N donor and an O$^-$ group selected from the group consisting of 8-hydroxy quinoline, 2-hydroxy pyridine, 2-(2-hydroxy ethyl)pyridine, pyridyl-2-, piperidyl-2-, quinolyl-2-, isoquinolyl-1- and isoquinolyl-3-carboxylates, particulaly pyridyl-2-carboxylate, piperidyl-2 carboxylate, and 8-hydroxyquinoline.

In another embodiment of the invention, the sulfonated phosphorous ligand in the compound of formula I is a sulfonated mono phosphine.

In a further embodiment of the invention, the sulfonated phosporous ligand is selected from the group consisting of tris(sodium-3-sulfonatophenyl)phosphine(TPPTS), phenyl bis(sodium-3-sulfonatophenyl)phosphine(TPPDS), diphenyl(sodium-3-sulfonatophenyl) phosphine(TPPMS), methylbis(3-sulfonatophenyl)phosphine, cyclohexylbis (sodium-3-sulfonato phenyl)phosphine, isopropylbis (sodium-3-sulfonatophenyl)phosphine, dimethyl (sodium-3-sulfonatophenyl) phosphine, dicyclohexyl-(3-sulfonatophenyl)phosphine.

In another embodiment of the invention, the amount of the sulfonated phosphine ligand used per gram mole of palladium for the preparation of the palladium complex of formula I is 1–10 moles, preferably 2–3 moles.

In still another embodiment the organic solvent used for the preparation of the palladium complex of formula I is selected from the group consisting of chloroform, dichloromethane and methyl ethyl ketone.

In still another embodiment the alcohol solvent used for the precipitation of the palladium complex of formula I from the aqueous layer is selected from methanol and ethanol.

In another embodiment the silica used for the preparation of the supported aqueous phase catalyst containing the complex of formula I is selected from porous or non-porous silica.

In another embodiment the silica for the preparation of the supported aqueous phase catalyst containing the complex of formula I is preferably dehydroxylated by heating at 523 K under vacuum for 5–6 hours.

DETAILED DESCRIPTION OF THE INVENTION

Although many water soluble palladium complexes have been reported in the literature, the water soluble complex having the formula I and the corresponding supported aqueous phase catalysts have been synthesised for the first time and there is no prior art available for synthesising these complexes and supported aqueous phase catalysts thereof.

The process of the present invention described herein below with reference to examples, which are illustrative only and should not be construed to limit the scope of the present invention in any manner.

EXAMPLE 1

0.0629 mmol of the palladium complex of formula II wherein $R'_1$, $R'_2$, $R'_3$=phenyl, X=p-toluenesulfonato(TsO$^-$),

=pyridyl-2-carboxylate (prepared as the procedure given in the patent U.S. Pat. No. 6,069,253)} was dissolved in methyl ethyl ketone (MEK) (10 ml) and shaken vigorously with 3 equivalents of TPPTS {tris(m-sulfophenyl)phosphine trisodium salt} in degassed water (6 ml). The yellow colour of the MEK layer disappeared and the aqueous layer. became yellow in colour indicating the formation of the palladium complex of formula I in water, which was precipitated from water by adding methanol. The yellow fine suspension of the compound I was filtered under argon, washed with methanol and dried under vacuum to yield a yellow fine powder. Yield=90% Anal. Calcd. for $C_{31}H_{23}N Na_3O_{14}PPdS_4.6H_2O$: C, 34.598; H, 3.278; N, 1.301; S, 11.916; P, 2.878; Found: C,34.05; H, 3.28; N, 1.33; S, 12.32; P, 2.50. IR (KBr) 1636 s ($v_{c=o}$), 1397s ($v_{o=c-o}$), 524s ($v_{Pd-N}$). $^{31}$p ($D_2O$, ppm) δ 35.3 Is (N trans to P), δ 36.13w (N cis. to P). $^1$H ($D_2O$, ppm) δ 2.25 s (3H, tolyl $CH_3$), δ 7.2-8 m (Ph and pyridil).

EXAMPLE 2

0.0629 mmol of the palladium complex of formula II wherein $R'_1$, $R'_2$ $R'_3$=phenyl, X=p-toluenesulfonato(TsO$^-$),

=pyridyl-2-carboxylate (prepared as the procedure given in the patent U.S. Pat. No. 6,069,253)} was dissolved in chloroform (10 ml) and shaken vigorously with 3 equivalents of TPPTS {tris(m-sulfophenyl)phosphine trisodium salt} in degassed water (6 ml). The yellow colour of the chloroform layer disappeared and the aqueous layer became yellow in colour indicating the formation of the palladium complex of formula I, which was precipitated from water by adding methanol. The yellow fine suspension of the compound I was filtered under argon, washed with methanol and dried under vacuum to yield a yellow fine powder. Yield= 92%

EXAMPLE 3

0.0629 mmol of the palladium complex of formula IIa {II in which $R'_1$, $R'_2$, $R'_3$=phenyl, X=p-toluenesulfonato(TsO$^-$),

=pyridyl-2-carboxylate (prepared as the procedure given in the patent U.S. Pat. No. 6,069,253)} was dissolved in methyl ethyl ketone (MEK) (10 ml) and shaken vigorously with 3 equivalents of TPPTS {tris(m-sulfophenyl)phosphine trisodium salt} in degassed water (6 ml). The yellow colour of the MEK layer disappeared and the aqueous layer became yellow in colour indicating the formation of the palladium complex of formula I, which was precipitated from water by adding ethanol. The yellow fine suspension of the compound I was filtered under argon, washed with ethanol and dried under vacuum to yield a yellow fine powder. Yield=90%

EXAMPLE 4

0.0629 mmol of the palladium complex of formula II wherein $R'_1$, $R'_2$ $R'_3$=phenyl, X=p-toluenesulfonato(TsO$^-$),

=pyridyl-2-carboxylate (prepared as the procedure given in the patent U.S. Pat. No. 6,069,253)} was dissolved in methyl ethyl ketone (MEK) (10 ml) and shaken vigorously with 2 equivalents of TPPTS {tris(m-sulfophenyl)phosphine trisodium salt} in degassed water (6 ml). The yellow colour of the MEK layer disappeared and the aqueous layer became yellow in colour indicating the formation of the palladium complex of formula I, which was precipitated from water by adding methanol. The yellow fine suspension of the compound I was filtered under argon, washed with methanol and dried under vacuum to yield a yellow fine powder. Yield= 88%

EXAMPLE 5

0.0629 mmol of the palladium complex of formula II wherein $R'_1$, $R'_2$, $R'_3$=phenyl, X=p-toluenesulfonato(TsO$^-$),

=pyridyl-2-carboxylate (prepared as the procedure given in the patent U.S. Pat. No. 6,069,253)} was dissolved in methyl ethyl ketone (MEK) (10 ml) and shaken vigorously with I equivalent of TPPTS {tris(m-sulfophenyl)phosphine trisodium salt} in degassed water (6 ml). The yellow colour of the MEK layer disappeared and the aqueous layer became yellow in colour indicating the formation of the palladium complex of formula I, which was precipitated from water by adding methanol. The yellow fine suspension of the compound I was filtered under argon, washed with methanol and dried under vacuum to yield a yellow fine powder. Yield= 85%

EXAMPLE 6

0.0937 mmol of the palladium complex of formula II wherein R'$_1$, R'$_2$, R'$_3$=phenyl, X=p-toluenesulfonato(TsO$^-$),

=pyridyl-2carboxylate (prepared as the procedure given in the patent U.S. Pat. No. 6,069,253)} was dissolved in methyl ethyl ketone (MEK) (7 ml) and shaken vigorously with 3 equivalents of TPPTS {tris(m-sulfophenyl)phosphine trisodium salt} in degassed water (3 ml). The yellow colour of the MEK layer disappeared and the aqueous layer became yellow in colour indicating the formation of the palladium complex of formula I, in water which was added to 1 g of the dehydroxylated silica in a Schlenk flask and the wet solid was stirred for 2 h under argon. Water was then evaporated under high vacuum at constant stirring. A dry yellow powder was obtained which was stored under argon.

EXAMPLE 7

0.1874 mmol of the palladium complex of formula II wherein R'$_1$, R'$_2$, R'$_3$=phenyl, X=p-toluenesulfonato(TsO$^-$),

=pyridyl-2-carboxylate (prepared as the procedure given in the patent U.S. Pat. No. 6,069,253)} was dissolved in methyl ethyl ketone (MEK) (7 ml) and shaken vigorously with 3 equivalents of TPPTS {tris(m-sulfophenyl)phosphine trisodium salt} in degassed water (3 ml). The yellow colour of the MEK layer disappeared and the aqueous layer became yellow in colour indicating the formation of the palladium complex of formula I, in water which was added to 1 g of the dehydroxylated silica in a Schlenk flask and the wet solid was stirred for 2 h under argon. Water was then evaporated under high vacuum at constant stirring. A dry yellow powder was obtained which was stored under argon.

EXAMPLE 8

0.04685 mmol of the palladium complex of formula II wherein R'$_1$, R'$_2$1 R'$_3$=phenyl, X=p-toluenesulfonato(TsO$^-$),

=pyridyl-2-carboxylate (prepared as the procedure given in the patent U.S. Pat. No. 6,069,253)} was dissolved in methyl ethyl ketone (MEK) (7 ml) and shaken vigorously with 3 equivalents of TPPTS {tris(m-sulfophenyl)phosphine trisodium salt} in degassed water (3 ml). The yellow colour of the MEK layer disappeared and the aqueous layer became yellow in colour indicating the formation of the palladium complex of formula I in water which was added to 1 g of the dehydroxylated silica in a Schlenk flask and the wet solid was stirred for 2 h under argon. Water was then evaporated under high vacuum at constant stirring. A dry yellow powder was obtained which was stored under argon.

ADVANTAGES OF PRESENT INVENTION

1. Invention of novel water-soluble palladium complexes and supported aqueous phase catalysts thereof which are stable and may be useful catalysts for a variety of organic transformations such as carbonylation, oxidation, hydrogenation, coupling, alkylation, oligomerization, polymerisation etc.

2. An easy single step process for the synthesis of novel water soluble palladium complexes with high yield.

We claim:

1. A water soluble palladium complex of the general formula I

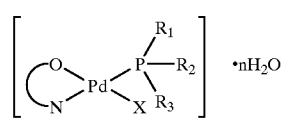

Formula I wherein R$_1$, R$_2$, R$_3$ are substituents on phosphine ligands selected from the group consisting of hydrogen, alkyl, arylalkyl, and cycloaliphatic at least one of which carries a sulfonic acid, and salts thereof, X is aryl or alkyl sulphonato or aryl or alkyl carboxylato or formato or halides such as Cl$^-$, Br$^-$, I$^-$,

is an anionic chelating ligand consisting of an N donor and a O$^-$ group, 1<n<10.

2. A process for the preparation of water soluble palladium complexes having general formula I,

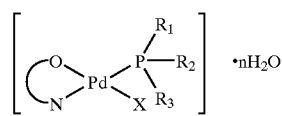

Formula I wherein R$_1$, R$_2$, R$_3$ are substituents on phosphine ligands selected from the group consisting of hydrogen, alkyl, arylalkyl, and cycloaliphatic at least one of which carries a sulfonic acid, and salts there of, X is aryl or alkyl sulphonato or aryl or alkyl carboxylato or formato or halides such as Cl$^-$, Br$^-$, I$^-$,

is an anionic chelating ligand consisting of an N donor and a O$^-$group, 1<n<10, said process comprising reacting a palladium compound of formula II

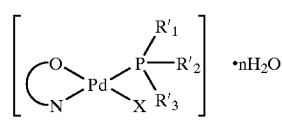

Formula I wherein R'$_1$, R'$_2$ and R'$_3$ are substituents on the phosphine ligand such as, alkyl, aryl, arylalkyl, cycloaliphatic, X is aryl or alkyl sulfonato or aryl or alkyl carboxylate or formato or halides such as Cl⁻, Br⁻, I⁻,

is an anionic chelating ligand containing a N donor and O⁻group, in an organic solvent with a sulfonated phosphine ligand in degassed water to form the palladium complex of formula I in water, separating the aqueous layer and precipitating the complex of formula I by adding an alcohol solvent.

3. A process as claimed in claim 2 wherein the precipitated complex of formula I is converted into the supported aqueous phase form by mixing the aqueous layer containing the water soluble palladium complex of formula I with dehydroxylated silica in a Schlenk flask, forming a wet solid, stirring the wet solid vigorously for 2 h under argon, evaporating water under high vacuum at constant stirring to obtain the supported aqueous phase catalyst containing the palladium complex of the formula I as a dry yellow powder.

4. A process as claimed in claim 2 wherein the anionic chelating ligand in the compounds of formula I and II is an organic compound, containing a N donor and an O⁻group selected from the group consisting of 8-hydroxy quinoline, 2-hydroxy pyridine, 2-(2-hydroxy ethyl)pyridine, pyridyl-2-, piperidyl-2-, quinolyl-2-, isoquinolyl-1- and isoquinolyl-3-carboxylates, particulaly pyridyl-2-carboxylate, piperidyl-2-carboxylate, and 8-hydroxyquinoline.

5. A process as claimed in claim 2 wherein the sulfonated phosphorous ligand in the compound of formula I is a sulfonated mono phosphine.

6. A process as claimed in claim 5 wherein the sulfonated phosporous ligand is selected from the group consisting of tris(sodium-3-sulfonatophenyl)phosphine(TPPTS), phenyl bis(sodium-3-sulfonatophenyl)phosphine(TPPDS), diphenyl(sodium-3-sulfonatophenyl) phosphine(TPPMS), methylbis(3-sulfonatophenyl)phosphine, cyclohexylbis (sodium-3-sulfonato phenyl)phosphine, isopropylbis (sodium-3-sulfonatophenyl)phosphine, dimethyl (sodium-3-sulfonatophenyl)phosphine, and dicyclohexyl-(3-sulfonatophenyl)phosphine.

7. A process as claimed in claim 2 wherein the amount of the sulfonated phosphine ligand used per gram mole of palladium for the preparation of the palladium complex of formula I is 1–10 moles.

8. A process as claimed in claim 7 wherein the amount of the sulfonated phosphine ligand used per gram mole of palladium for the preparation of the palladium complex of formula I is 2–3 moles.

9. A process as claimed in claim 2 wherein the organic solvent used for the preparation of the palladium complex of formula I is selected from the group consisting of chloroform, dichloromethane and methyl ethyl ketone.

10. A process as claimed in claim 2 wherein the alcohol solvent used for the precipitation of the palladium complex of formula I from the aqueous layer is selected from methanol and ethanol.

11. A process as claimed in claim 3 wherein the silica used for the preparation of the supported aqueous phase catalyst containing the complex of formula I is selected from porous or non-porous silica.

12. A process as claimed in claim 3 wherein the silica for the preparation of the supported aqueous phase catalyst containing the complex of formula I is dehydroxylated by heating at 523 K under vacuum for 5–6 hours.

13. A process as claimed in claim 2 wherein the precipitated complex of formula I is converted into the supported aqueous phase form by mixing the aqueous layer containing the water soluble palladium complex of formula I with dehydroxylated silica to form a wet solid, stirring the wet solid vigorously for 2 h under argon, evaporating water under high vacuum at constant stirring to obtain the supported aqueous phase catalyst containing the palladium complex of the formula I as a dry powder.

14. The complex according to claim 1 wherein the halide is selected from the group consisting of Cl⁻, Br⁻ and I⁻.

15. The complex according to claim 2 wherein the halide is selected from the group consisting of Cl⁻, Br⁻ and I⁻.

* * * * *